(12) United States Patent
Ke et al.

(10) Patent No.: US 11,813,379 B2
(45) Date of Patent: Nov. 14, 2023

(54) STERILIZATION AND DISINFECTION LAMP

(71) Applicant: CE LIGHTING LTD., Shenzhen (CN)

(72) Inventors: Ping Ke, Shenzhen (CN); Dangwei Yang, Shenzhen (CN)

(73) Assignee: CE LIGHTING LTD., Shenzhen (CN)

( * ) Notice: Subject to any disclaimer, the term of this patent is extended or adjusted under 35 U.S.C. 154(b) by 391 days.

(21) Appl. No.: 16/934,622

(22) Filed: Jul. 21, 2020

(65) Prior Publication Data

US 2021/0402043 A1 Dec. 30, 2021

(30) Foreign Application Priority Data

Jun. 30, 2020 (CN) .......................... 202010614675.0
Jun. 30, 2020 (CN) .......................... 202021250333.7

(51) Int. Cl.
*A61L 9/20* (2006.01)

(52) U.S. Cl.
CPC ............. *A61L 9/20* (2013.01); *A61L 2209/12* (2013.01); *A61L 2209/134* (2013.01); *A61L 2209/14* (2013.01)

(58) Field of Classification Search
CPC ................................ A61L 9/20; A61L 2209/14
See application file for complete search history.

(56) References Cited

U.S. PATENT DOCUMENTS

| | | | | |
|---|---|---|---|---|
| 5,330,722 A | * | 7/1994 | Pick .......................... | A61L 9/16 250/492.1 |
| 2006/0201119 A1 | * | 9/2006 | Song .................... | B01D 53/007 55/471 |
| 2008/0019861 A1 | * | 1/2008 | Silderhuis ................. | A61L 9/16 422/4 |
| 2010/0095844 A1 | * | 4/2010 | Gilleland .................. | A61L 9/20 96/16 |

* cited by examiner

*Primary Examiner* — Kevin Joyner
(74) *Attorney, Agent, or Firm* — LEASON ELLIS LLP

(57) ABSTRACT

A sterilizing lamp comprises a lamp body module having an air inlet and an air outlet at the-bottom and top of the module, respectively, a circuit board module, an ultraviolet light emitting device, a fan and a filter screen bracket. The filter screen bracket wraps and covers the ultraviolet light emitting device. An airflow channel opening is arranged on the filter screen bracket. An air filtering device is wrapped on the filter screen bracket to cover the airflow channel opening. The outside air is suctioned by the fan into the module and is filtered by the air filtering device and then is discharged from the air outlet. When the air passes through the air filtering device fine particulate matter are filtered and retained by the air filtering device, and are irradiated for sterilization in the ultraviolet light emitting device.

9 Claims, 12 Drawing Sheets

STERILIZATION AND DISINFECTION LAMP

TECHNICAL FIELD

The present invention relates to a sterilizing apparatus, particularly to a sterilizing lamp.

BACKGROUND ART

The pathogens or viruses of many diseases can be spread in the air, infectious diseases in particular, posing a serious threat to human life and health. In recent years, the outbreaks of Severe Acute Respiratory Syndrome (SARS), Middle East Respiratory Syndrome (MERS), and novel coronavirus pneumonia have sounded alarm bells to mankind. The existing methods to eliminate viruses and bacteria in the air are limited, mainly including sprinkling, that is, chemical disinfectant (powder) is spread into the air through vaporized spray or sprinkling, but this method is prone to excessive disinfection. It is not advisable to directly spray disinfectant (powder) on people's whole bodies, or use chemical disinfectants to disinfect indoor air when people are in the room because chemical disinfectants are harmful to the human body. Another way to disinfect indoor air is disinfection through direct irradiation by ultraviolet fluorescent lamps. However, during disinfection in this way, no one can stay in the room in order to prevent ultraviolet rays from causing damage to human eyes, skin, etc., and this way of sterilization will generate ozone, which is also harmful to the human body. Therefore, this method cannot achieve real-time work in a human environment. Once it stops working, the indoor air quality will quickly return to the level before purification, and its sterilization and detoxification effects will disappear. Therefore, how to scientifically and effectively kill viruses and bacteria in the air and purify the air is an important topic.

SUMMARY OF THE INVENTION

A technical problem that the present invention intends to solve is to overcome the defects of the prior art and provide a sterilizing lamp that can work continuously, is used conveniently, prevents ultraviolet leakage, is safe and harmless to the human body and can purify the indoor air when people are in the room.

The present invention adopts the following technical solution: The sterilizing lamp provided by the present invention comprises a lamp body module; the lamp body module is provided with an air inlet and an air outlet at the top and bottom of the lamp body module respectively, and internally provided with a circuit board module, an ultraviolet light emitting device, a fan and a filter screen bracket; the filter screen bracket wraps and covers the ultraviolet light emitting device; an airflow channel opening is arranged on the filter screen bracket; an air filtering device is wrapped on the filter screen bracket to cover the airflow channel opening; the circuit board module is electrically connected to the ultraviolet light emitting device and the fan respectively; the fan is used for sucking outside air from the air inlet into an inner cavity of the filter screen bracket, which passes the airflow channel opening, is filtered by the air filtering device and then is discharged from the air outlet; and when the air passes through the air filtering device, viruses, bacteria and fine particulate matter are filtered and retained by the air filtering device and irradiated for sterilization in the ultraviolet light emitting device.

The lamp body module comprises a lower casing, an upper casing and a base; the lower casing is matched with and connected to a side wall of the upper casing in a sealable manner; the bottom of the filter screen bracket is provided with a ribbed buckle; the lower casing is internally provided with a buckle seat; a resilient buckle and a bayonet are arranged on the base; after being inserted into the bayonet, the ribbed buckle is rotated to an angle and retained and fixed by an edge of the bayonet so that the filter screen bracket is connected and fixed to the base; and the resilient buckle is matched and fixed with the buckle seat in a buckled manner so that the base is connected to the lower casing in a detachable manner.

After the base is connected and fixed to the lower casing, the air inlet in a ring shape is formed between the outer edge of the base and the bottom margin of the lower casing and leads into an inner cavity of the filter screen bracket and meanwhile, the filter screen bracket isolates the inner cavity of the lower casing from the outside world and the air outlet is located at the top of the upper casing.

The lamp body module is internally provided with an inner support, the top of the inner support is provided with a first bolt hole, a side wall of the fan is provided with a second bolt hole, the upper casing is internally provided with a first stud, and the fan is clamped between the top of the inner support and the first stud, and is connected to the first stud through a screw after the screw passes through the first bolt hole and the second bolt hole in turn so as to connect and fix the inner support and the fan.

The bottom of the inner support is provided with a second stud, the lower casing is internally provided with a third bolt hole and is connected to the second stud through a screw after the screw passes through the third bolt hole so that the lower casing is connected and fixed to the inner support, and meanwhile the upper part of the filter screen bracket stretches into an inner cavity of the inner support.

The ultraviolet light emitting device is an ultraviolet bulb, and the sterilizing lamp further comprises a lamp holder, which is fixed on the base.

The bottom of the lower casing is provided with a hitch ring.

The lower casing is pervious to light and an LED lamp is arranged on the circuit board module and emits light via the lower casing.

The air filtering device adopts a multi-layer filter screen or melt blown fabric.

The fan is an axial flow fan.

The sterilizing lamp further comprises a power supply interface to supply power to the circuit board module, the ultraviolet light emitting device and the fan from an external power supply.

The sterilizing lamp further comprises wall-mounted accessories, including a power box, a connector and a bottom bracket; the power box is internally provided with a switching power supply; connecting holes used for mounting to a wall are arranged on the connector; the power box is connected to the connector and the bottom bracket respectively; the front end of the bottom bracket is provided with a hook portion; the front surface of the power box is a curve surface on which a plug connected to an output end of the switching power supply is arranged; the shape of the curve surface is matched with the shape of the outer side wall of the lamp body module; when the lamp body module is connected to the wall-mounted accessories, the curve surface is fit with the outer side wall of the lamp body module, and the plug is matched with and plugged into the power supply interface and conducts electricity to supply power to the circuit board module, the ultraviolet light emitting device and the fan from the switching power supply; and the hook portion is clipped into the air inlet and is used for supporting and hooking the lamp body module.

Alternatively, the sterilizing lamp further comprises wall-mounted accessories, including a wall-mounted bracket and a connector; the wall-mounted bracket is internally provided with a switching power supply; connecting holes used for mounting to a wall are arranged on the connector; the wall-mounted bracket is fixed and connected to the connector and the lamp body module by means of screws; the front surface of the wall-mounted bracket is provided with a plug connected to an output end of the switching power supply; the shape of the front surface of the wall-mounted bracket is matched with the shape of the outer side wall of the lamp body module; and when the lamp body module is connected to the wall-mounted accessories, the front surface of the wall-mounted bracket is fit with the outer side wall of the lamp body module and the plug is matched with and plugged into the power supply interface and conducts electricity to supply power to the circuit board module, the ultraviolet light emitting device and the fan from the switching power supply.

Beneficial effects of the present invention: The sterilizing lamp provided by the present invention comprises a lamp body module; the lamp body module is provided with an air inlet and an air outlet at the top and bottom of the lamp body module respectively, and internally provided with a circuit board module, an ultraviolet light emitting device, a fan and a filter screen bracket; the filter screen bracket wraps and covers the ultraviolet light emitting device; an airflow channel opening is arranged on the filter screen bracket; an air filtering device is wrapped on the filter screen bracket to cover the airflow channel opening; the circuit board module is electrically connected to the ultraviolet light emitting device and the fan respectively; the fan is used for sucking outside air from the air inlet into an inner cavity of the filter screen bracket, which passes the airflow channel opening, is filtered by the air filtering device and then is discharged from the air outlet; and when the air passes through the air filtering device, viruses, bacteria and fine particulate matter are filtered and retained by the air filtering device and irradiated for sterilization in the ultraviolet light emitting device. The present invention overcomes the defects and deficiencies of the prior art, and a built-in fan is used to input outside air from the air inlet and output the air from the air outlet so that indoor air is circulated continuously. When the air passes through the air filtering device, viruses, bacteria and fine particulate matter are retained, dust, bacteria and viruses of above PM2.5 can be filtered, and the ultraviolet light emitting device provides persistent irradiation for a sufficient time and the time of effective irradiation and sterilization is long enough to kill the bacteria and viruses in the air filtering device and achieve the air purifying effect; further, the covering and sheltering of the filter screen bracket, the air filtering device and the lamp body module blocks ultraviolet light from emitting out of the lamp body module, completely avoiding leakage of ultraviolent light. The sterilizing lamp can achieve indoor sterilization safely when some people are in the room, and purify the air in real time even during sleep in a bedroom; therefore, the present invention is a sterilizing lamp that can work continuously, is used conveniently, prevents ultraviolet leakage, is safe and harmless to the human body and can purify the indoor air when people are in the room.

The sterilizing lamp further comprises wall-mounted accessories, including a power box, a connector and a bottom bracket; the power box is internally provided with a switching power supply; connecting holes used for mounting to a wall are arranged on the connector; the power box and the bottom bracket are connected to the connector respectively; the front end of the bottom bracket is provided with a hook portion; the front surface of the power box is a curve surface on which a plug connected to an output end of the switching power supply is arranged; the shape of the curve surface is matched with the shape of the outer side wall of the lamp body module; when the lamp body module is connected to the wall-mounted accessories, the curve surface is fit with the outer side wall of the lamp body module, and the plug is matched with and plugged into the power supply interface and conducts electricity to supply power to the circuit board module, the ultraviolet light emitting device and the fan from the switching power supply; and the hook portion is clipped into the air inlet and is used for supporting and hooking the lamp body module. When the sterilizing lamp provided by the present invention is connected to the lamp body module by means of the wall-mounted accessories, the sterilizing lamp not only realizes structural connection in a clever manner, and is used as a wall lamp under the condition of no change in the structure of the lamp body module, but also makes circuit connection coherent, and the overall appearance harmonious. When the sterilizing lamp does not need to be used as a wall lamp, the lamp body module can be taken down and used in other forms such as a table lamp, a bed lamp or a ceiling lamp, thereby achieving multiple uses of one lamp, cost reduction and convenient use.

In the same way, the sterilizing lamp further comprises wall-mounted accessories, including a wall-mounted bracket and a connector; the wall-mounted bracket is internally provided with a switching power supply; connecting holes used for mounting to a wall are arranged on the connector; the wall-mounted bracket is fixed and connected to the connector and the lamp body module by means of screws; the front surface of the wall-mounted bracket is provided with a plug connected to an output end of the switching power supply; the shape of the front surface of the wall-mounted bracket is matched with the shape of the outer side wall of the lamp body module; and when the lamp body module is connected to the wall-mounted accessories, the front surface of the wall-mounted bracket is fit with the outer side wall of the lamp body module and the plug is matched with and plugged into the power supply interface and conducts electricity to supply power to the circuit board module, the ultraviolet light emitting device and the fan from the switching power supply. When the sterilizing lamp provided by the present invention is connected to the lamp body module by means of the wall-mounted accessories, the sterilizing lamp not only realizes structural connection in a clever manner, and is turned into a wall lamp under the condition of no change in the structure of the lamp body module, but also makes circuit connection coherent and the overall appearance harmonious, facilitates disassembly and use and reduces cost.

DETAILED DESCRIPTION

Embodiment 1

Figure 1:
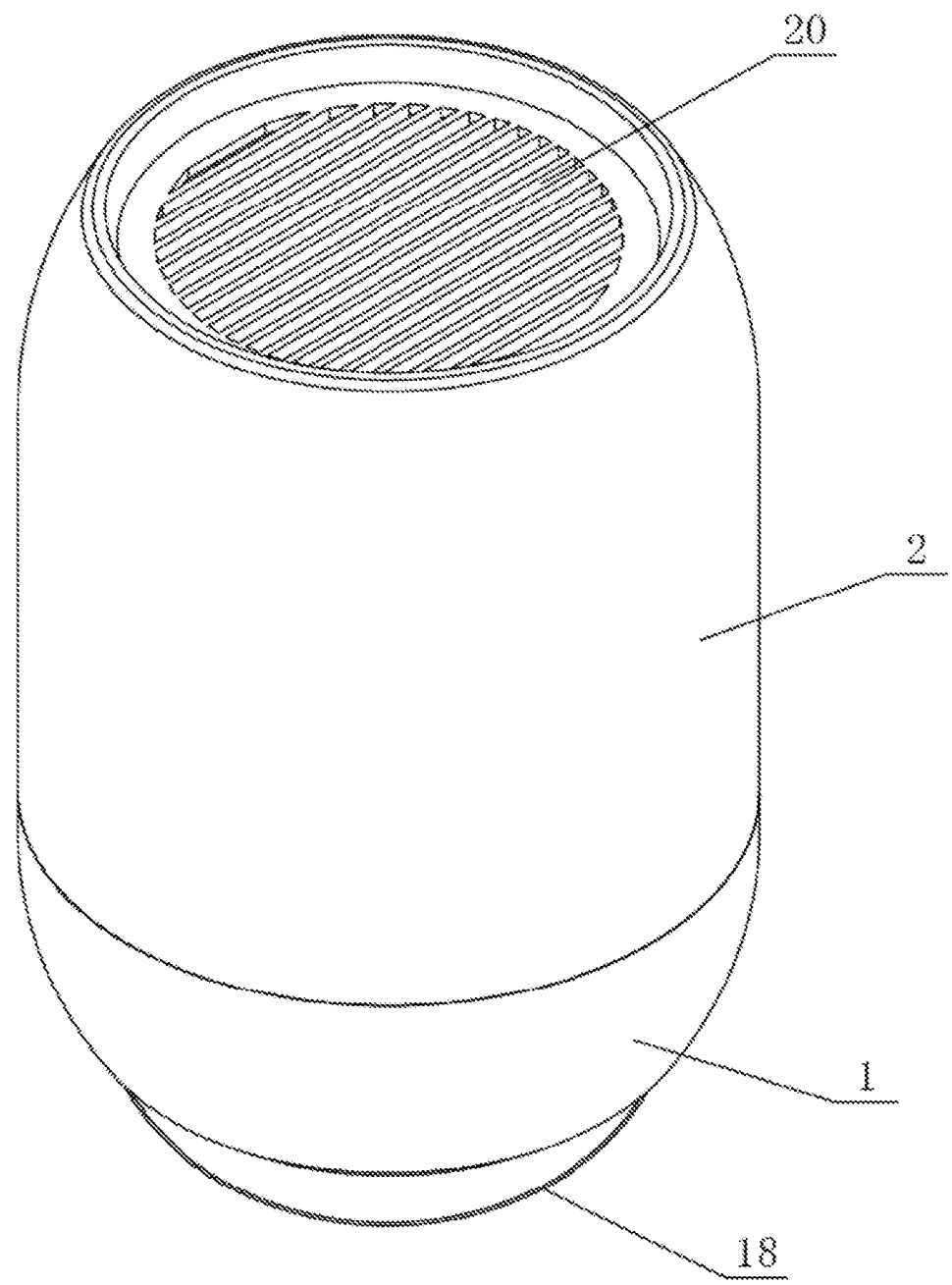
FIG. 1 is an overall structural schematic view of a sterilizing lamp in embodiment 1 of the present invention.
Figure 2:
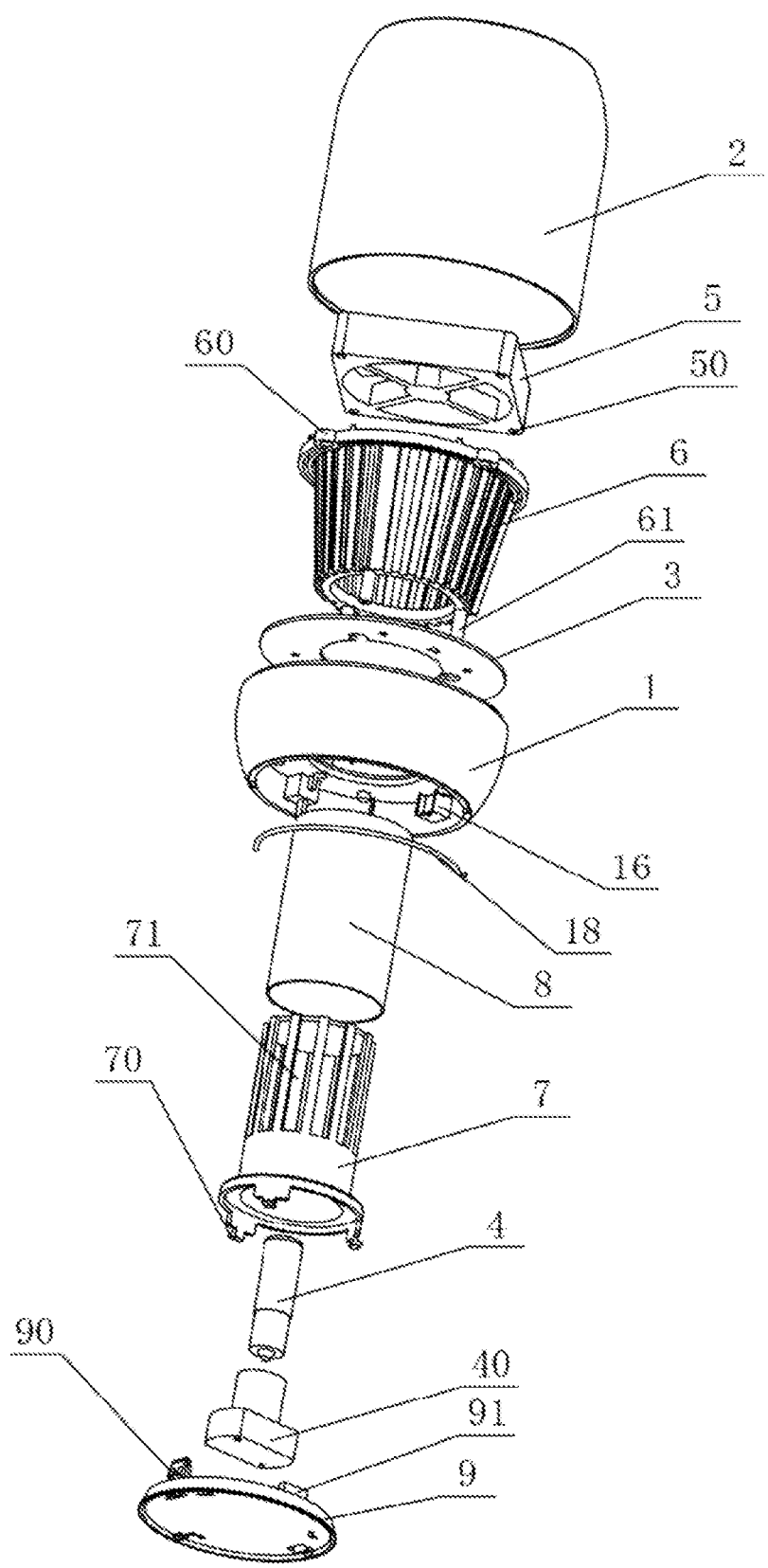
FIG. 2 is an exploded structural schematic view of a sterilizing lamp in embodiment 1 of the present invention.
Figure 3:
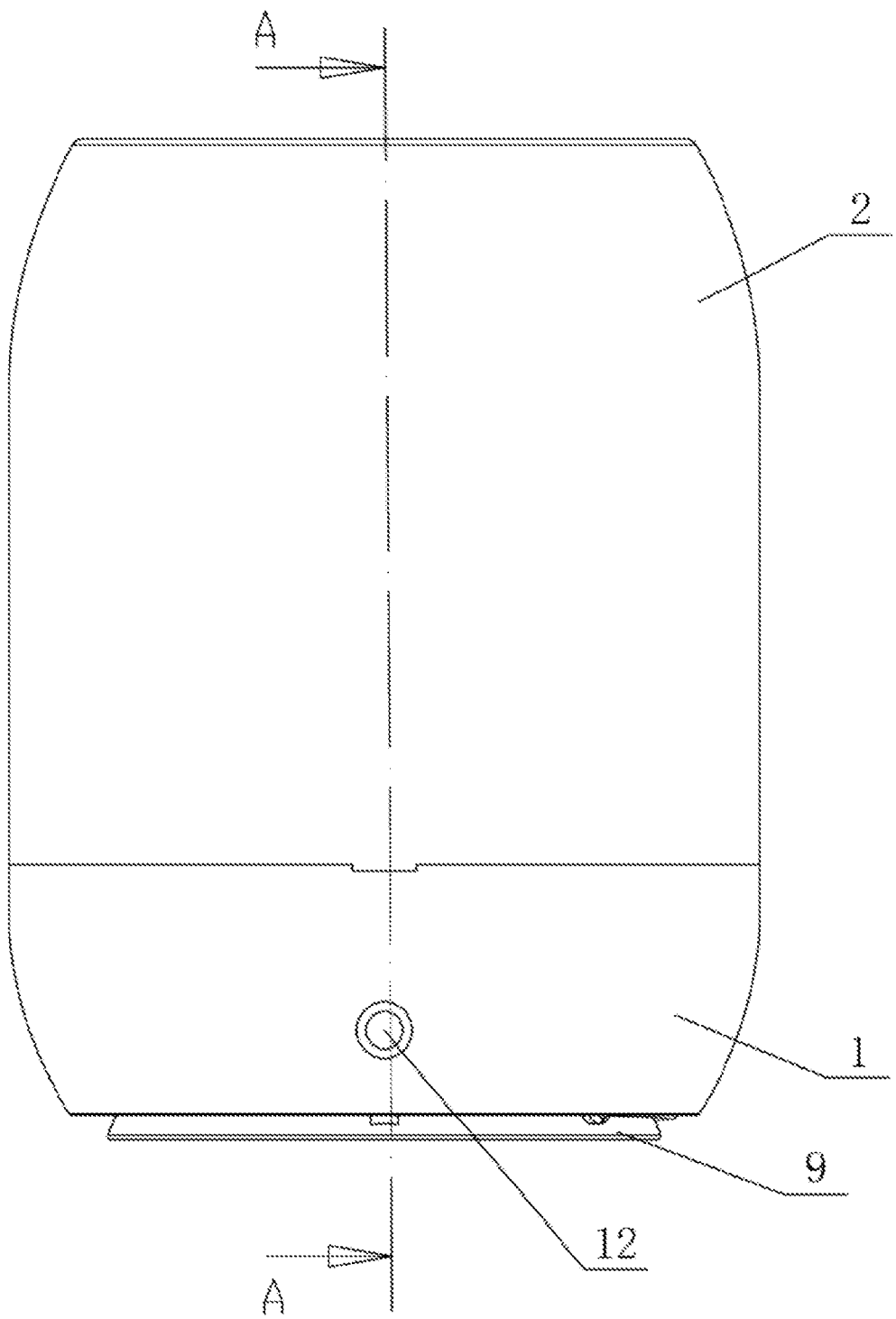
FIG. 3 is a structural schematic side view of a sterilizing lamp in embodiment 1 of the present invention.
Figure 4:
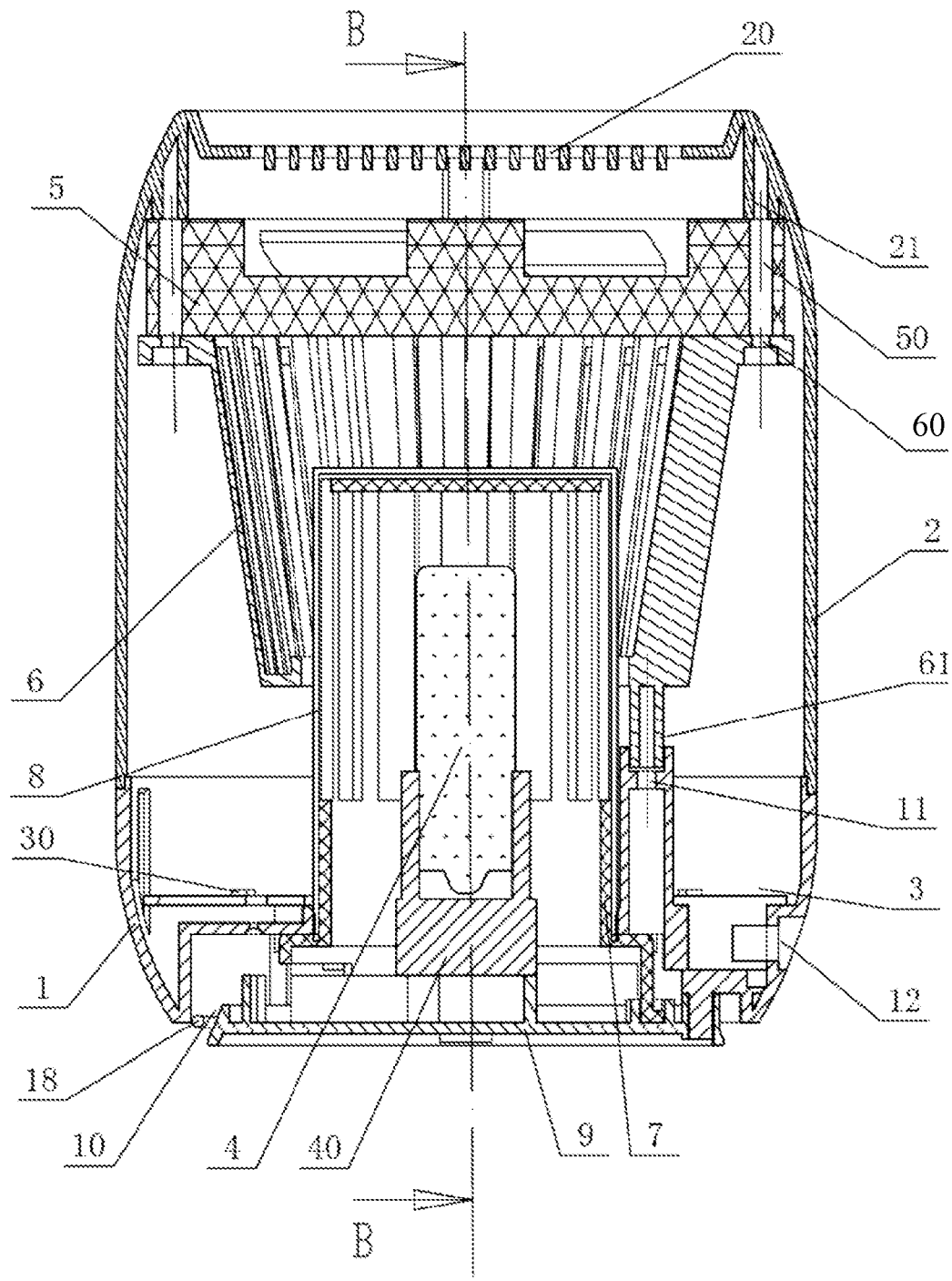
FIG. 4 is a structural schematic view of section A-A in FIG. 3.
Figure 5:
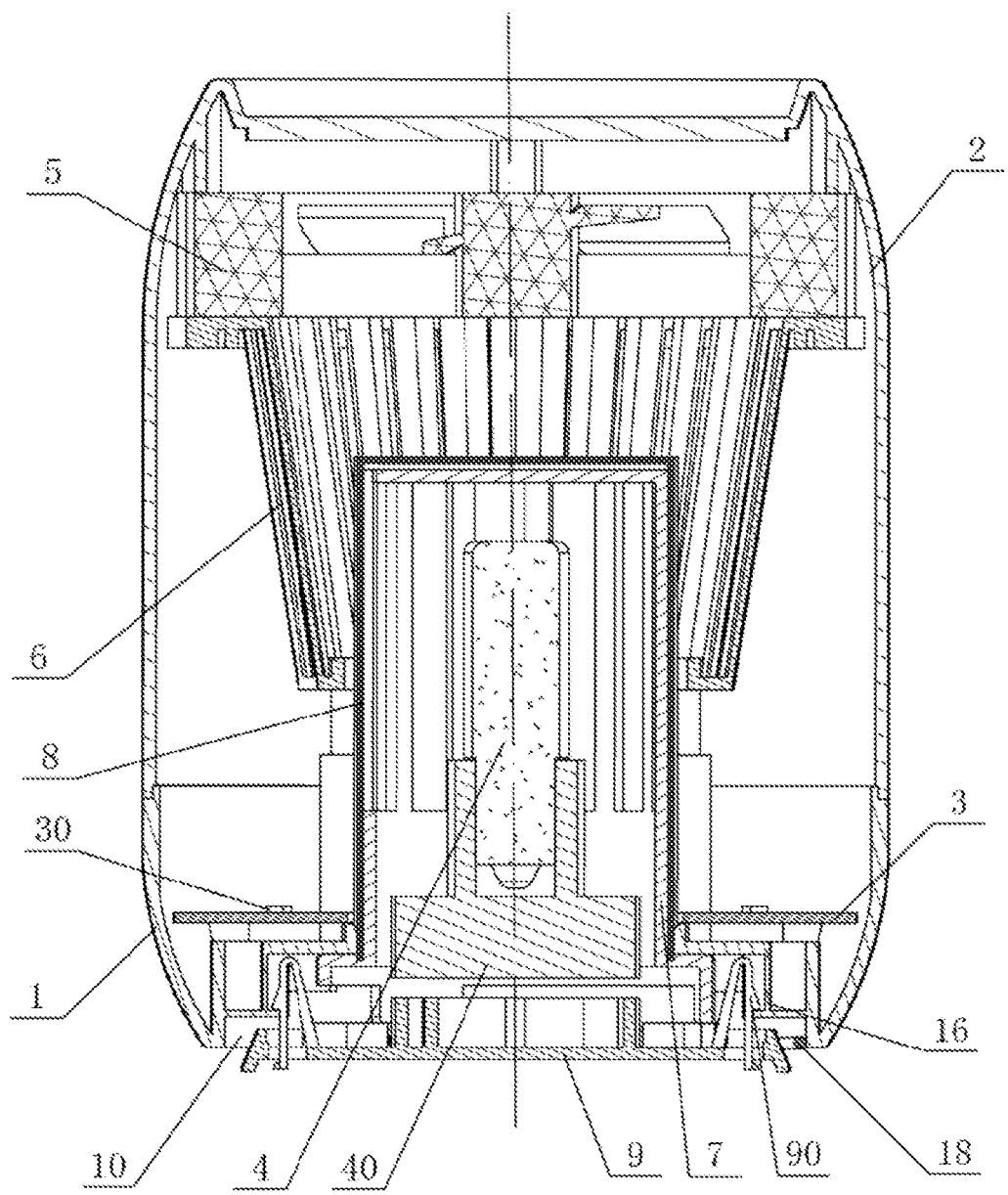
FIG. 5 is a structural schematic view of section B-B in FIG. 4.
Figure 6:
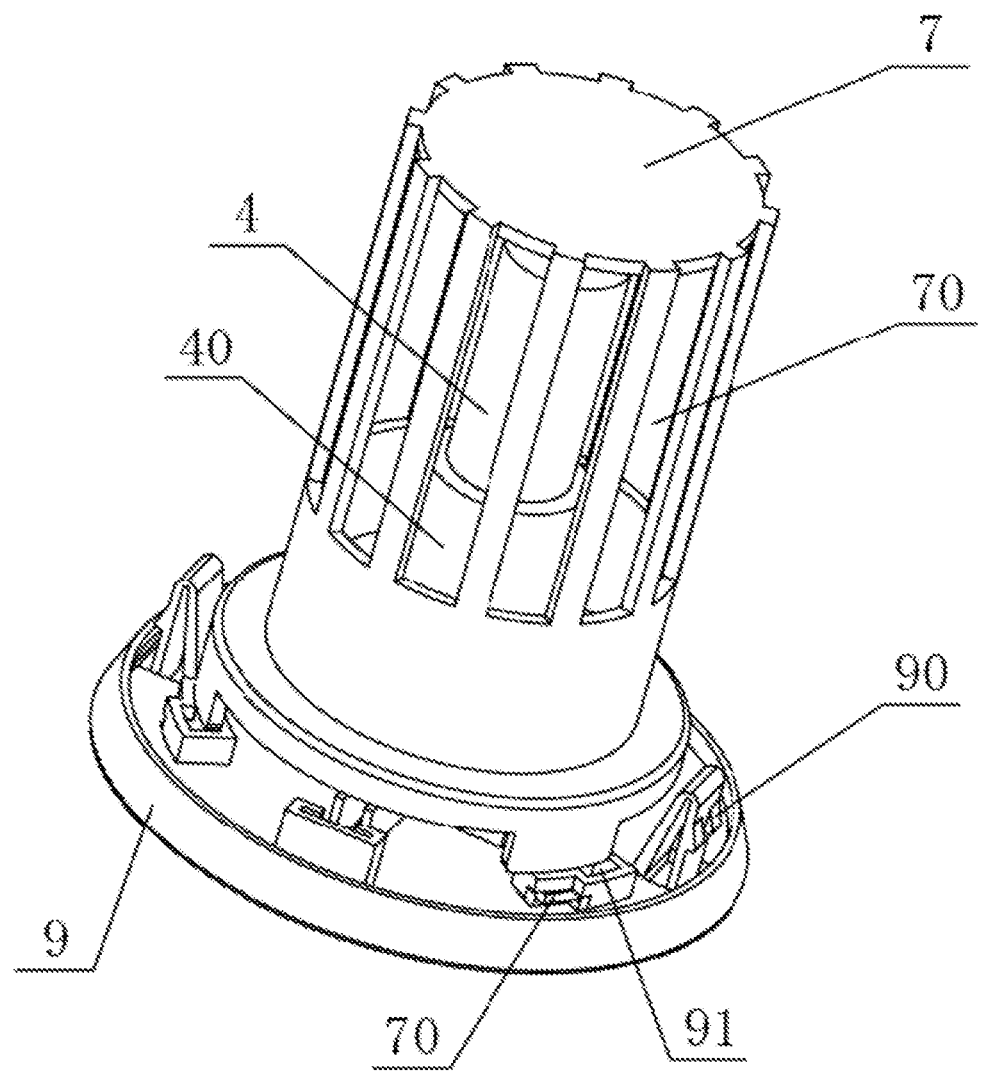
FIG. 6 is a structural schematic view of a connection between a filter screen bracket and a base of a sterilizing lamp in embodiment 1 of the present invention.

As shown in FIG. 1 to FIG. 6, the sterilizing lamp in this embodiment can be used in such forms as a table lamp, a bed lamp and a camping lamp, and comprises a lamp body module; the lamp body module is provided with an air inlet 10 and an air outlet 20 at the bottom and top of the lamp body module, respectively, and internally provided with a circuit board module 3, an ultraviolet light emitting device 4, a fan 5 and a filter screen bracket 7; the filter screen bracket 7 wraps and covers the ultraviolet light emitting device 4. An airflow channel opening 71 is arranged on the filter screen bracket 7. An air filtering device 8 is wrapped on the filter screen bracket 7 to cover the airflow channel opening 71. The circuit board module 3 is electrically connected to the ultraviolet light emitting device 4 and the fan 5, respectively. The fan 5 is used for sucking outside air from the air inlet 10 into an inner cavity of the filter screen bracket 7, which passes the airflow channel opening 71, is filtered by the air filtering device 8 and then is discharged from the air outlet 20. When the air passes through the air filtering device 8, viruses, bacteria and fine particulate matter are filtered and retained by the air filtering device 8 and irradiated for sterilization in the ultraviolet light emitting device 4. The air filtering device 8 adopts a multi-layer filter screen or melt blown fabric, has low cost and is suitable for regular replacement.

Specifically, the lamp body module comprises a lower casing 1, an upper casing 2 and a base 9; the lower casing 1 is matched with and connected to a side wall of the upper casing 2 in a sealable manner; the bottom of the filter screen bracket 7 is provided with a ribbed buckle 70; the lower casing 1 is internally provided with a buckle seat 16; a resilient buckle 90 and a bayonet 91 are arranged on the base 9; after being inserted into the bayonet 91, the ribbed buckle 70 is rotated to an angle and retained and fixed by an edge of the bayonet 91 so that the filter screen bracket 7 is connected and fixed to the base 9; the resilient buckle 90 is matched and fixed with the buckle seat 16 in a buckled manner so that the base 9 is connected to the lower casing 1 in a detachable manner to make for installation, disassembly, and replacement of the ultraviolet light emitting device 4, the air filtering device 8 and other consumables, and for cleanup; after the base 9 is fixed and connected to the lower casing 1, the air inlet 10 in a ring shape is formed between the outer edge of the base 9 and the bottom margin of the lower casing 1 and leads into an inner cavity of the filter screen bracket 7; and meanwhile, the filter screen bracket 7 isolates the inner cavity of the lower casing 1 from the outside world, and the air outlet 20 is located at the top of the upper casing 2. In this embodiment, the ultraviolet light emitting device 4 is an ultraviolet bulb, the sterilizing lamp further comprises a lamp holder 40, which is fixed on the base 9, the ultraviolet bulb only generates a tiny amount of ozone and meanwhile, ozone can be adsorbed by the air filtering device 8, so it will not do harm to the human body. In this embodiment, the bottom of the lower casing 1 is provided with a hitch ring 18 to facilitate hooking. When hooking is not needed, the hitch ring 18 can be received in the air inlet 10 at the bottom of the lower casing 1. This use is convenient. In addition, the hitch ring 18 can be hooked to a rope to hang the sterilizing lamp in this embodiment and used in the form of ceiling lamp; the lower casing 1 is pervious to light; an LED lamp 30 is arranged on the circuit board module 3 and emits light via the lower casing 1; the upper casing 2 can be pervious to light or not pervious to light; and the LED lamp 30 can illuminate the lamp body module, and achieve the purpose of atmosphere lighting and decoration. Of course, it can be directly used for ordinary functional lighting.

The lamp body module is further provided with an inner support 6 internally; the top of the inner support 6 is provided with a first bolt hole 60; a side wall of the fan 5 is provided with a second bolt hole 50; the upper casing 2 is internally provided with a first stud 21; the fan 5 is clamped between the top of the inner support 6 and the first stud 21, and is connected to the first stud 21 through a screw after the screw passes through the first bolt hole 60 and the second bolt hole 50 in turn so as to connect and fix the inner support 6 and the fan 5; the bottom of the inner support 6 is provided with a second stud 61; the lower casing 1 is internally provided with a third bolt hole 11 and is connected to the second stud 61 through a screw after the screw passes through the third bolt hole 11 so that the lower casing 1 is connected and fixed to the inner support 6; and meanwhile the upper part of the filter screen bracket 7 stretches into an inner cavity of the inner support 6 so that the fan 5 directly sucks the air in the inner cavity of the filter screen bracket 7 through the inner cavity of the inner support 6. In this embodiment, the fan 5 is a silent fan and adopts an axial flow fan.

The sterilizing lamp further comprises a power supply interface 12 to supply power to the circuit board module 3, the ultraviolet light emitting device 4 and the fan 5 from an external power supply such as a power adapter or a power bank.

Principle of this embodiment: The lower casing 1 and the upper casing 2 constitute a confined space. The internal air can be discharged only by the fan 5 passively, external air can be sucked in only from the bottom of the air inlet 10, and during work, the fan 5 keeps discharging internal air, and forces the external air to be sucked in from the bottom. In this way, when viruses and bacteria pass the airflow channel opening 71, they are blocked on the inner side of the air filtering device 8, and are killed in the ultraviolet light emitting device 4. The operation is circulated to achieve the purpose of sterilizing indoor air.

Embodiment 2

Figure 7:
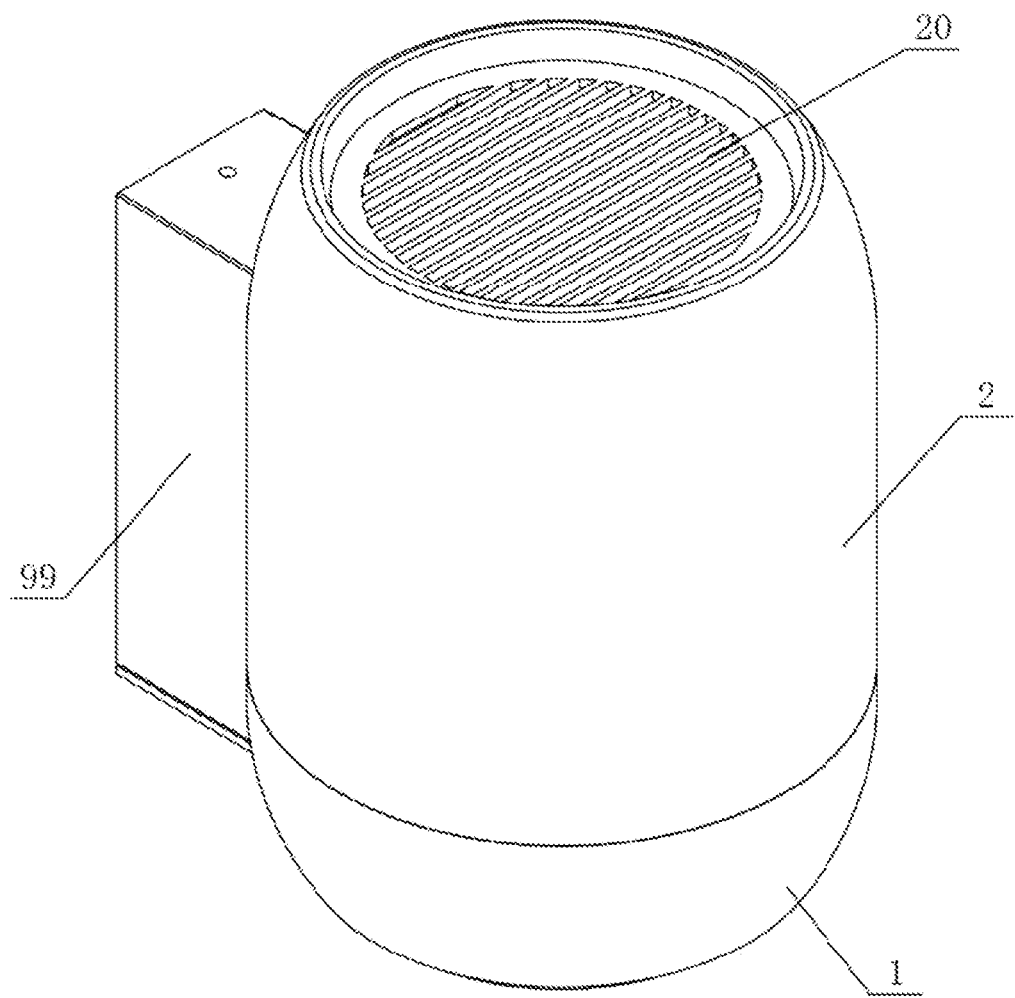
FIG. 7 is an overall structural schematic diagram of a sterilizing lamp in embodiment 2 of the present invention.
Figure 8:
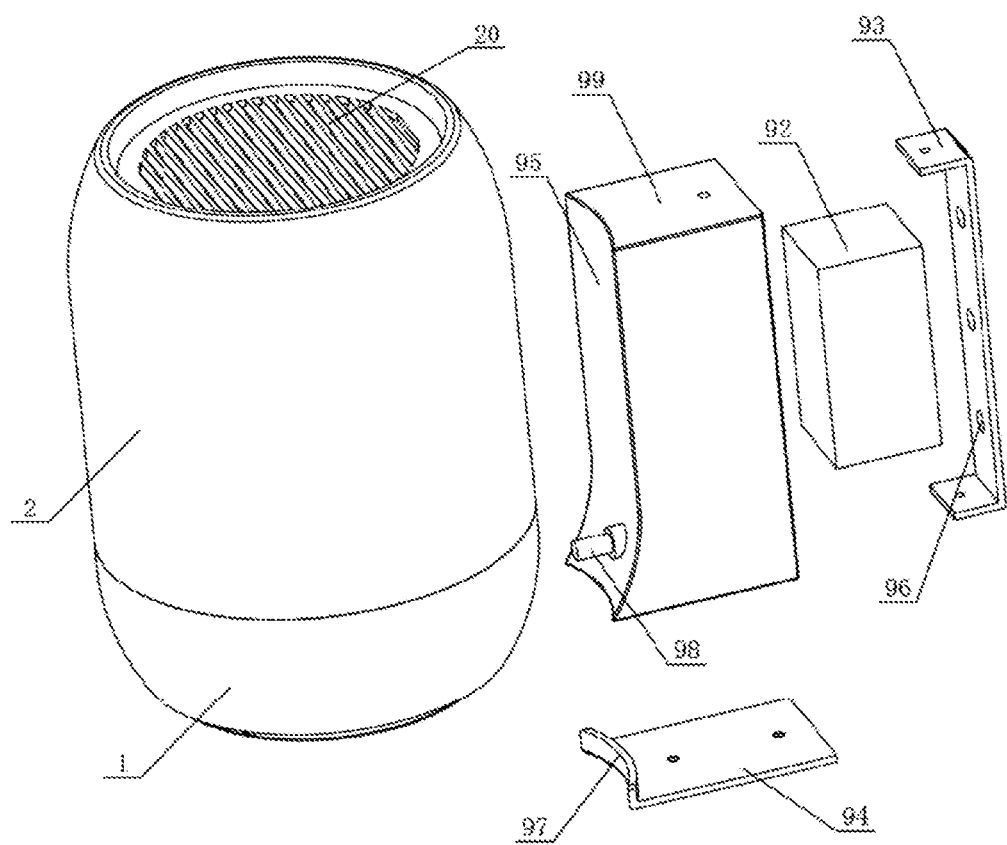
FIG. 8 is an exploded structural schematic view of components of a sterilizing lamp in embodiment 2 of the present invention.
Figure 9:
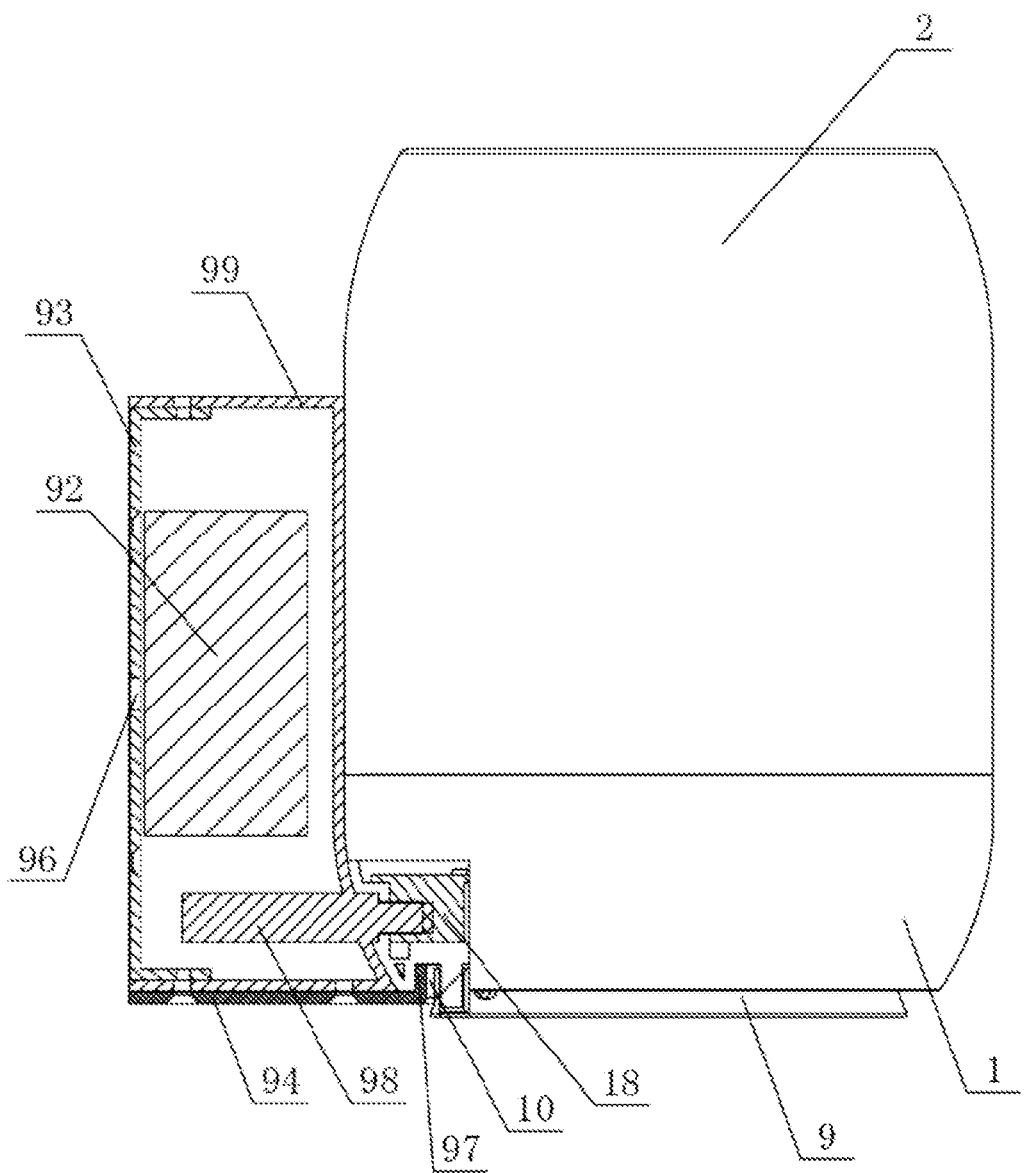
FIG. 9 is a partial sectional structural schematic view of a sterilizing lamp in embodiment 2 of the present invention.

As shown in FIG. 7 to FIG. 9, this embodiment has the following difference from embodiment 1: on the basis of embodiment 1, the sterilizing lamp in this embodiment further comprises wall-mounted accessories, including a power box 99, a connector 93 and a bottom bracket 94; the power box 99 is internally provided with a switching power supply 92; connecting holes 96 used for mounting to a wall are arranged on the connector 93; the power box 99 is connected to the connector 93 and the bottom bracket 94 by means of screws respectively; the front end of the bottom bracket 94 is provided with a hook portion 97; the front surface of the power box 99 is a curve surface 95; on the curve surface 95, a plug 98 connected to an output end of the switching power supply 92 is arranged; the shape of the curve surface 95 is matched with the shape of the outer side wall of the lamp body module; when the lamp body module is connected to the wall-mounted accessories, the curve surface 95 is fit with the outer side wall of the lamp body module, and the plug 98 is matched with and plugged into the power supply interface 12 and conducts electricity to supply power to the circuit board module 3, the ultraviolet light emitting device 4 and the fan 5 from the switching power supply 92; and the hook portion 97 is clipped into the air inlet 10 and is used for supporting and hooking the lamp body module.

When the sterilizing lamp in this embodiment is connected to the lamp body module by means of the wall-mounted accessories, it not only realizes structural connection with the lamp body module in a clever manner, and is turned into a wall lamp under the condition of no change in the structure of the lamp body module, but also makes circuit connection coherent, and the overall appearance harmonious. When the sterilizing lamp does not need to be used as a wall lamp, the lamp body module can be taken down and used in other forms such as a table lamp, a bed lamp or a ceiling lamp (i.e., form of embodiment 1), thereby achieving multiple uses of one lamp, cost reduction and convenient use.

Other characteristics of this embodiment are the same as those of embodiment 1.

Embodiment 3

Figure 10:
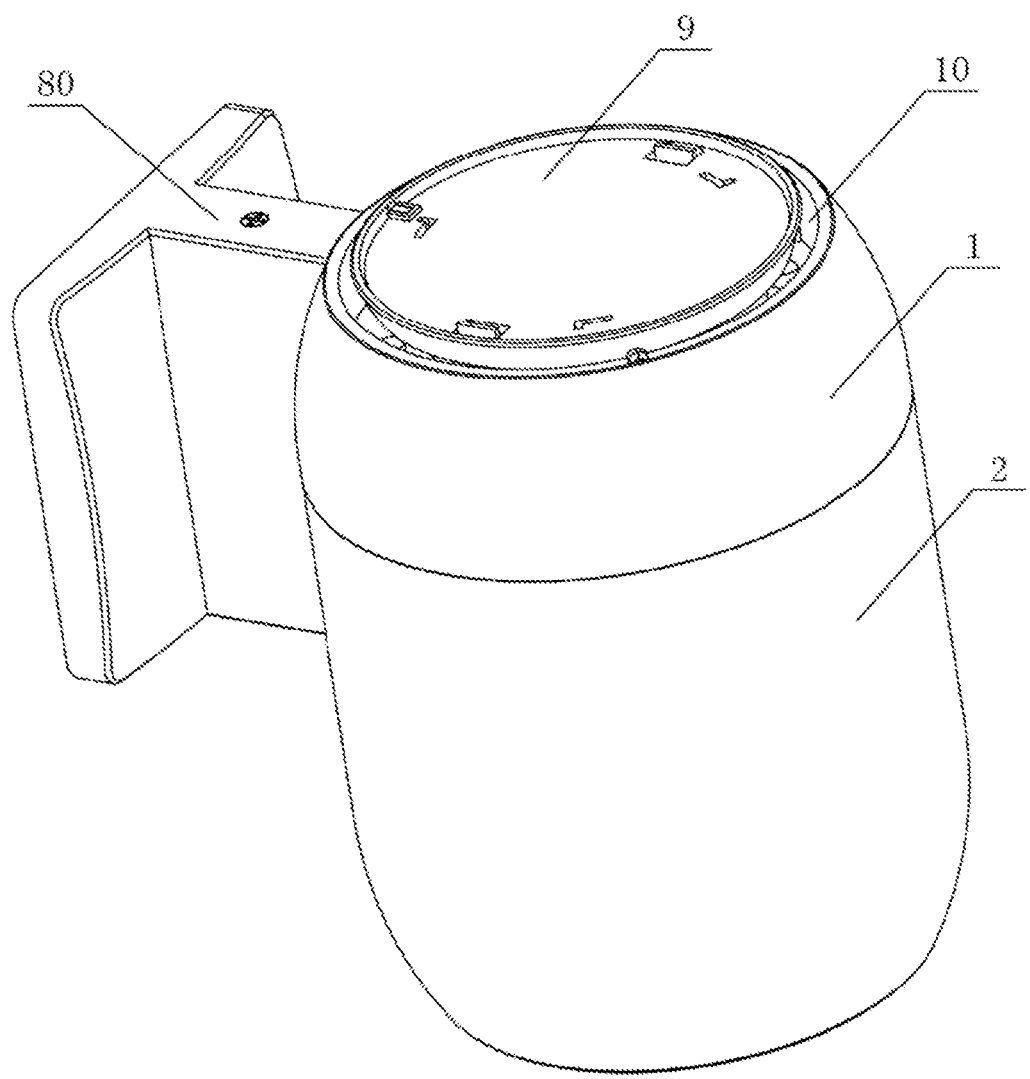
FIG. 10 is an overall structural schematic diagram of a sterilizing lamp in embodiment 3 of the present invention.
Figure 11:
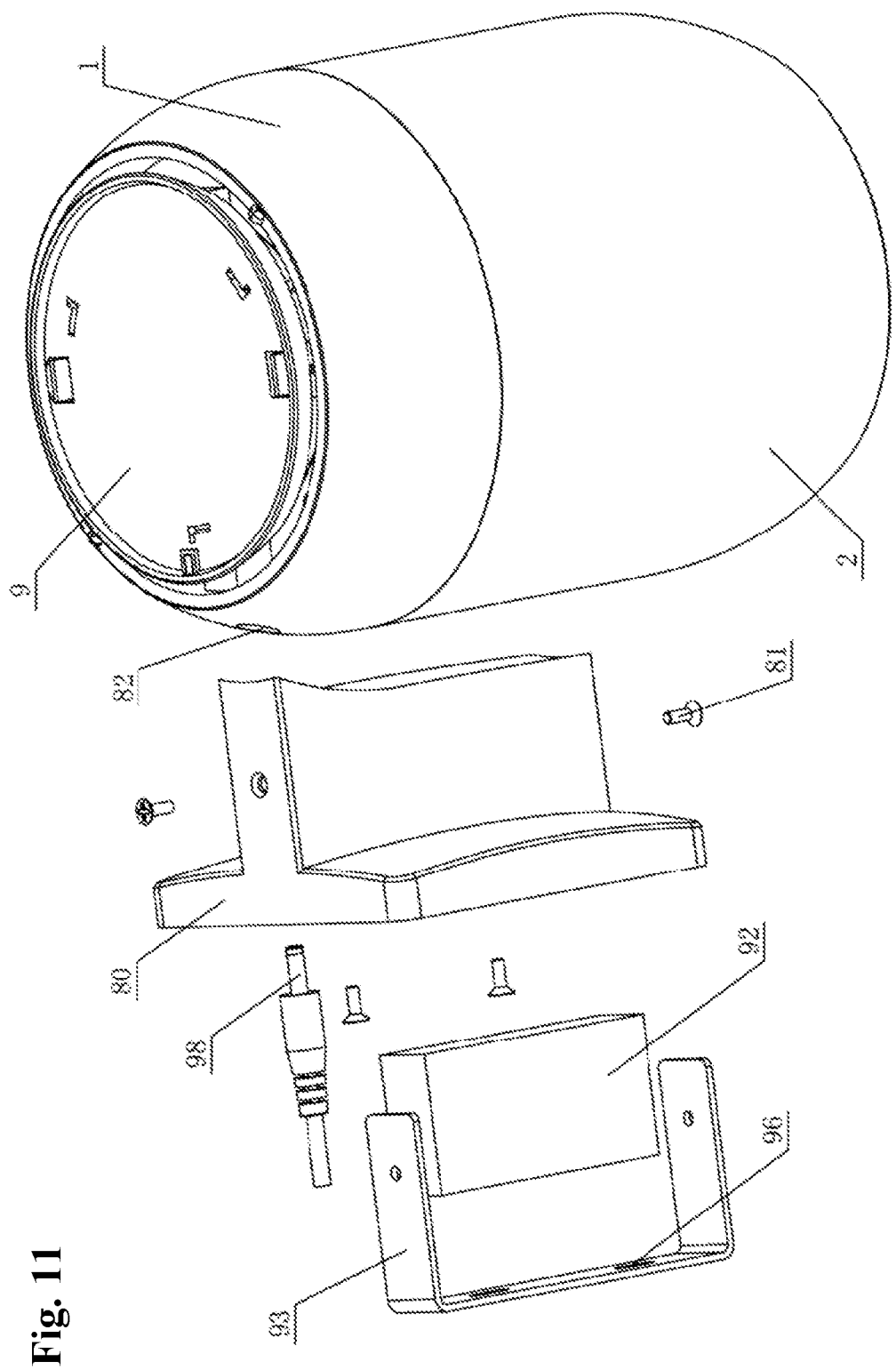
FIG. 11 is an exploded structural schematic view of components of a sterilizing lamp in embodiment 3 of the present invention.
Figure 12:
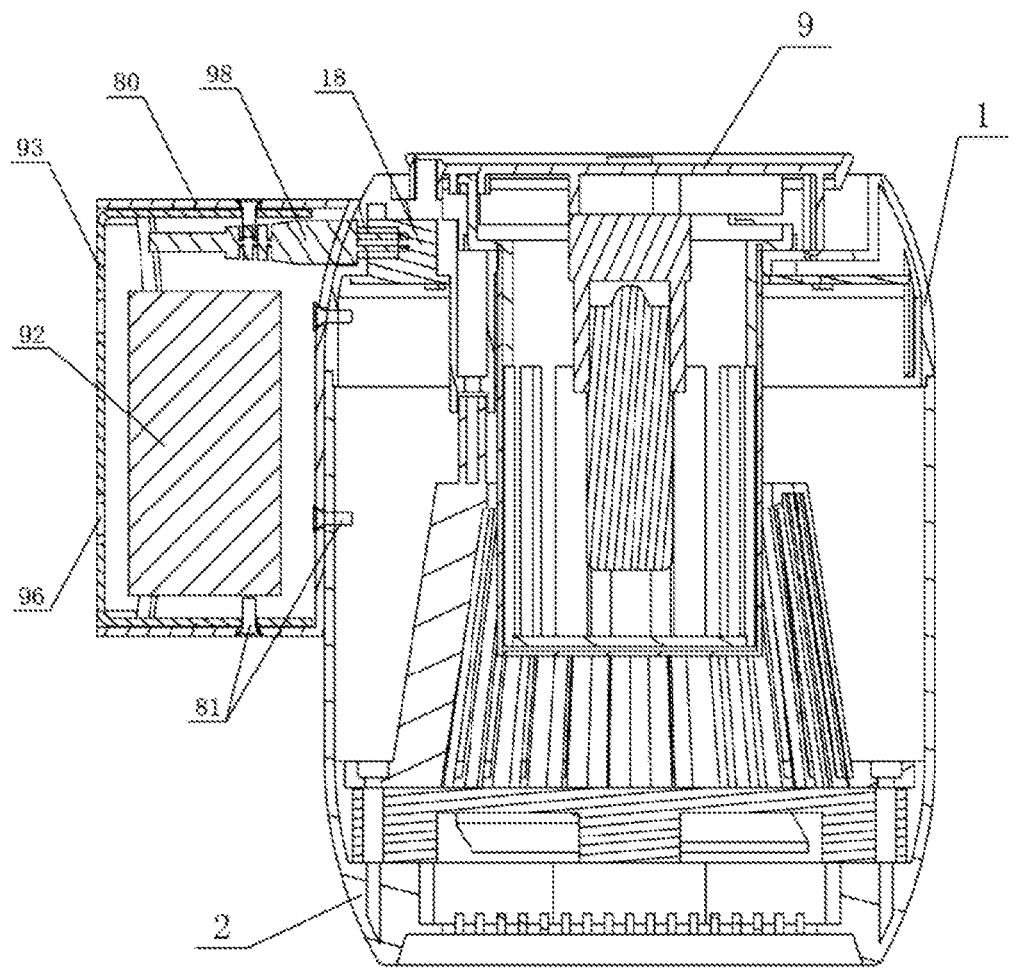
FIG. 12 is a partial sectional structural schematic view of a sterilizing lamp in embodiment 3 of the present invention.

As shown in FIG. 10 to FIG. 12, this embodiment has the following difference from embodiment 1: on the basis of embodiment 1, the sterilizing lamp of this embodiment further comprises wall-mounted accessories, including a wall-mounted bracket 80 and a connector 93; the wall-mounted bracket 80 is internally provided with a switching power supply 92; connecting holes 96 used for mounting to a wall are arranged on the connector 93; the wall-mounted bracket 80 is fixed and connected to the connector 93 and the lamp body module by means of a screw 81; a screw hole 82 allowing the screw 81 to pass through is arranged on a side wall of the lamp body module; the front surface of the wall-mounted bracket 80 is provided with a plug 98 connected to an output end of the switching power supply 92; the shape of the front surface of the wall-mounted bracket 80 is matched with the shape of the outer side wall of the lamp body module; and when the lamp body module is connected to the wall-mounted accessories, the front surface of the wall-mounted bracket 80 is fit with the outer side wall of the lamp body module, and the plug 98 is matched with and plugged into the power supply interface 12 and conducts electricity to supply power to the circuit board module 3, the ultraviolet light emitting device 4 and the fan 5 from the switching power supply 92. In this embodiment, the lamp body module is placed upside down, in other words, the lower casing 1 is at the top and the upper casing 2 is at the bottom. Of course, they can be placed in a normal direction as in embodiment 2.

When the sterilizing lamp in this embodiment is connected to the lamp body module by means of the wall-mounted accessories, it not only realizes structural connection with the lamp body module in a clever manner, and is turned into a wall lamp under the condition of no change in the structure of the lamp body module, but also makes circuit connection coherent and the overall appearance harmonious, facilitates disassembly and use and saves cost.

Other characteristics of this embodiment are the same as those of embodiment 1.

The present invention overcomes the defects and deficiencies of the prior art, and a built-in fan 5 is used to input outside air from the air inlet 10 and output the air from the air outlet 20 so that indoor air is circulated continuously. When the air passes through the air filtering device 8, viruses, bacteria and fine particulate matter are retained, dust, bacteria and viruses of above PM2.5 can be filtered, and the ultraviolet light emitting device 4 provides persistent irradiation for a sufficient time and the time of effective irradiation and sterilization is long enough to kill the bacteria and viruses in the air filtering device 8 and achieve the air purifying effect; further, the covering and sheltering of the filter screen bracket 7, the air filtering device 8 and the lamp body module blocks ultraviolet light from emitting out of the lamp body module, completely avoiding leakage of ultraviolent light. The sterilizing lamp can achieve indoor sterilization safely when some people are in the room and purify the air in real time even during sleep in a bedroom; therefore, the present invention is a sterilizing lamp that can work continuously, is used conveniently, prevents ultraviolet leakage, is safe and harmless to the human body and can purify the indoor air when people are present.

The present invention can be widely applied to the air purification field.

What is claimed is:

1. A sterilizing lamp comprising:
   a lamp body module having a lower casing, an upper casing and a base wherein the lower casing is matched with and connected to a side wall of the upper casing in a sealable manner and further wherein the lamp body module is provided with an air inlet and an air outlet at the bottom and top of the lamp body module, respectively, and is internally provided with a circuit board module, an ultraviolet light emitting device, a fan and a filter screen bracket;
   the filter screen bracket wraps and covers the ultraviolet light emitting device;
   an airflow channel opening is arranged on the filter screen bracket to surround the ultraviolet light emitting device;
   an air filtering device is wrapped on the filter screen bracket to cover the airflow channel opening, wherein the bottom of the filter screen bracket is provided with a ribbed buckle, the lower casing is internally provided with a buckle seat, a resilient buckle and a bayonet are arranged on the base, and after being inserted into the bayonet, the ribbed buckle is rotated to an angle and retained and fixed by an edge of the bayonet so that the filter screen bracket is connected and fixed to the base; and the resilient buckle is matched and fixed with the buckle seat in a buckled manner so that the base is connected to the lower casing in a detachable manner;

the circuit board module is electrically connected to the ultraviolet light emitting device and the fan respectively;

the fan is used for sucking outside air from the air inlet into an inner cavity of the filter screen bracket, which passes the airflow channel opening, is filtered by the air filtering device and then is discharged from the air outlet; and when the air passes through the air filtering device, viruses, bacteria and fine particulate matter are filtered and retained by the air filtering device, and are irradiated for sterilization in the ultraviolet light emitting device.

2. The sterilizing lamp according to claim 1, wherein after the base is fixed and connected to the lower casing, the air inlet in a ring shape is formed between the outer edge of the base and the bottom margin of the lower casing and leads into an inner cavity of the filter screen bracket; and meanwhile the filter screen bracket isolates the inner cavity of the lower casing from the outside world, and the air outlet is located at the top of the upper casing.

3. The sterilizing lamp according to claim 1, wherein the lamp body module is also internally provided with an inner support; the top of the inner support is provided with a first bolt hole; a side wall of the fan is provided with a second bolt hole; the upper casing is internally provided with a first stud; and the fan is clamped between the top of the inner support and the first stud, and is connected to the first stud through a screw after the screw passes through the first bolt hole and the second bolt hole in turn so as to connect and fix the inner support and the fan.

4. The sterilizing lamp according to claim 3, wherein the bottom of the inner support is provided with a second stud; the lower casing is internally provided with a third bolt hole and is connected to the second stud through a screw after the screw passes through the third bolt hole so that the lower casing is connected and fixed to the inner support; and meanwhile the upper part of the filter screen bracket stretches into an inner cavity of the inner support.

5. The sterilizing lamp according to claim 1, wherein the ultraviolet light emitting device is an ultraviolet bulb; the sterilizing lamp further comprises a lamp holder, which is fixed on the base; the bottom of the lower casing is provided with a hitch ring; the lower casing is pervious to light; and an LED lamp is arranged on the circuit board module and emits light via the lower casing.

6. The sterilizing lamp according to claim 1, wherein the air filtering device adopts a multi-layer filter screen or melt blown fabric and the fan is an axial flow fan.

7. The sterilizing lamp according to claim 1, wherein the sterilizing lamp further comprises a power supply interface to supply power to the circuit board module, the ultraviolet light emitting device and the fan from an external power supply.

8. The sterilizing lamp according to claim 7, wherein the sterilizing lamp further comprises wall-mounted accessories, including a power box, a connector and a bottom bracket; the power box is internally provided with a switching power supply; connecting holes used for mounting to a wall are arranged on the connector (93); the power box is connected to the connector and the bottom bracket respectively; the front end of the bottom bracket is provided with a hook portion; the front surface of the power box is a curve surface on which a plug connected to an output end of the switching power supply is arranged; the shape of the curve surface is matched with the shape of the outer side wall of the lamp body module; when the lamp body module is connected to the wall-mounted accessories, the curve surface is fit with the outer side wall of the lamp body module, and the plug is matched with and plugged into the power supply interface and conducts electricity to supply power to the circuit board module, the ultraviolet light emitting device and the fan from the switching power supply; and the hook portion is clipped into the air inlet and is used for supporting and hooking the lamp body module.

9. The sterilizing lamp according to claim 7, wherein the sterilizing lamp further comprises wall-mounted accessories, including a wall-mounted bracket and a connector; the wall-mounted bracket is internally provided with a switching power supply; connecting holes used for mounting to a wall are arranged on the connector; the wall-mounted bracket is fixed and connected to the connector and the lamp body module by means of screws; the front surface of the wall-mounted bracket is provided with a plug connected to an output end of the switching power supply; the shape of the front surface of the wall-mounted bracket is matched with the shape of the outer side wall of the lamp body module; and when the lamp body module is connected to the wall-mounted accessories, the front surface of the wall-mounted bracket is fit with the outer side wall of the lamp body module and the plug is matched with and plugged into the power supply interface and conducts electricity to supply power to the circuit board module, the ultraviolet light emitting device and the fan from the switching power supply.

\* \* \* \* \*